United States Patent
Constantine et al.

(10) Patent No.: US 10,857,084 B2
(45) Date of Patent: Dec. 8, 2020

(54) COMPOSITION

(71) Applicant: COSMETIC WARRIORS LIMITED, Poole (GB)

(72) Inventors: Mark Constantine, Poole (GB); Margaret Joan Constantine, Poole (GB); Helen Elizabeth Ambrosen, Wimborne (GB); Rowena Jacqueline Bird, Christchurch (GB); Wesley Burrage, Poole (GB)

(73) Assignee: COSMETIC WARRIORS LIMITED, Poole (GB)

( * ) Notice: Subject to any disclaimer, the term of this patent is extended or adjusted under 35 U.S.C. 154(b) by 170 days.

(21) Appl. No.: 15/568,430

(22) PCT Filed: Apr. 21, 2016

(86) PCT No.: PCT/GB2016/051102
§ 371 (c)(1),
(2) Date: Oct. 20, 2017

(87) PCT Pub. No.: WO2016/170336
PCT Pub. Date: Oct. 27, 2016

(65) Prior Publication Data
US 2018/0104177 A1    Apr. 19, 2018

(30) Foreign Application Priority Data
Apr. 22, 2015 (GB) .................................. 1506827.3

(51) Int. Cl.
| A61K 8/00 | (2006.01) |
| A61K 8/46 | (2006.01) |
| A61K 8/73 | (2006.01) |
| A61Q 19/10 | (2006.01) |
| C11D 3/22 | (2006.01) |
| C11D 3/382 | (2006.01) |
| A61K 8/9794 | (2017.01) |
| A61K 8/9789 | (2017.01) |
| A61Q 5/02 | (2006.01) |

(52) U.S. Cl.
CPC ............. *A61K 8/463* (2013.01); *A61K 8/731* (2013.01); *A61K 8/9789* (2017.08); *A61K 8/9794* (2017.08); *A61Q 5/02* (2013.01); *A61Q 19/10* (2013.01); *C11D 3/222* (2013.01); *C11D 3/225* (2013.01); *C11D 3/382* (2013.01); *A61K 2800/31* (2013.01)

(58) Field of Classification Search
None
See application file for complete search history.

(56) References Cited

U.S. PATENT DOCUMENTS

| 9,370,478 B2 * | 6/2016 | Bonner ................... A61Q 5/12 |
| 9,629,790 B2 * | 4/2017 | Lundberg ............... A61K 8/731 |
| 2004/0254086 A1 * | 12/2004 | Hedges ................ A61K 8/0208 510/438 |

FOREIGN PATENT DOCUMENTS

| GB | 2503492 A | 1/2014 |
| WO | 2004/087857 A1 | 10/2004 |
| WO | 2013/175221 A2 | 11/2013 |
| WO | 2014/001806 A2 | 1/2014 |

OTHER PUBLICATIONS

International Search Report and Written Opinion for PCT/GB2016/051102, dated Jul. 5, 2016.
Search Report for British Patent Application No. 1506827.3, dated Jan. 28, 2016.
Mintel "Pink Grapefruit & Melon Glycerine Soap", Database GNPD: XP002723340 (2012).

* cited by examiner

*Primary Examiner* — Necholus Ogden, Jr.
(74) *Attorney, Agent, or Firm* — Merchant & Gould P.C.

(57) ABSTRACT

A solid surfactant cosmetic composition includes (i) insoluble vegetable fibre, insoluble fruit fibre or mixture thereof; (ii) surfactant; and (iii) hydrocolloid. The solid surfactant cosmetic composition is prepared by dehydrating a liquid composition. The liquid composition includes (i) a vegetable pulp containing insoluble vegetable fibre, a fruit pulp containing insoluble fruit fibre or a mixture thereof, wherein the vegetable pulp, fruit pulp or mixture thereof is in an amount of 55 to 99 wt. %; (ii) surfactant in an amount of 0.9 to 40 wt. %; and (iii) hydrocolloid in an amount of 0.1 to 15 wt. %, the amounts being based on the total combined amount of pulp, surfactant and hydrocolloid.

27 Claims, No Drawings

COMPOSITION

This application is a National Stage of PCT/GB2016/051102, filed 21 Apr. 2016, which claims benefit of British Patent Application No. 1506827.3, filed 22 Apr. 2015 which applications are incorporated herein by reference. To the extent appropriate, a claim of priority is made to each of the above disclosed applications.

FIELD OF THE INVENTION

The present invention relates to a solid product for use as a cosmetic, a process for producing said product, and a product prepared by the method.

BACKGROUND TO THE INVENTION

The present invention relates to products particularly those for use in contact with the human body.

For millennia soaps have been used for the purposes of washing the skin and clothes. The first known use of soap as a cleansing agent was in the ancient Babylonian period, approximately 2800BC, where soap formed from water, cinnamon oil and dissolved ashes was used to wash clothes and prepare wool for weaving. Egyptians also substantiated the use of soap derivatives, for the purposes of personal hygiene, medicinal applications and the effective washing of garments. However it was not until AD77 that Gaius Plinius Secundus (also known as Pliny the Elder) published his encyclopedic work, Historia Naturalis, whereby the first references to sapo (Latin for soap) were made. References were made to the manufacture of sapo, from tallow and ashes, whilst also describing its potential application as a pomade for hair.

The appeal of soap as a cleansing and personal hygiene agent grew. Although it was not until the 15th and 16th centuries, when soap production became semi-industrialised and the role it played in personal hygiene was understood, that soap became a universally accepted cleansing product in industrialised nations. However it was the First World War that prompted a shift in this trend, which resulted in the development of the first synthetic detergents, in response to a shortage of animal and vegetable fats used for making soap.

It is well known in the art that soap is effectively the salt of a fatty acid, resulting from the saponification of an animal or vegetable triglyceride using a strong base. Whilst soap is known to be an effective cleansing agent, soap can cause dryness and irritation to dry and sensitive skin. This is due to the basicity of soap and its cleansing action adversely affecting the cutaneous bacterial flora, enzyme activity in the upper epidermis and naturally occurring oils found on the skin and hair.

Synthetic detergents on the other hand can be synthesised in order to exhibit a wide variety of different properties that are particularly beneficial for their particular application. The desired properties of synthetic detergents used as skin or hair cleansers vary hugely from mild, conditioning surfactants to cleansers with high foaming abilities.

For cosmetic applications a synthetic detergent's potential is huge, ranging from shampoos and conditioners to facial cleaners and shower gels. During the 20th and 21st centuries these products have become staples of modern life in developed nations, available in a wide variety of physical forms. One form previously described has been for a 'paper' type sheet, as exemplified by WO/2014/001806, which refers to a readily dissolvable soap sheet. However this composition is unsuitable for the day-to-day cleansing of a user's skin or hair, which would typically be cleansed using a synthetic detergent. Previous examples of 'paper' type cosmetic products, comprising a synthetic detergents, have produced compositions that are typically fragile, flakeable materials or thick sheets. These synthetic detergent containing 'paper' type cosmetic products do not exhibit the flexibility of the sheets of WO 2014/001806 and have been found to be incapable of achieving the required specifications of a 'paper' type cosmetic sheet, e.g. foldable and pliable.

The present invention seeks to provide a solid surfactant cosmetic product which is foldable without snapping and which can be used in the manner of paper, for example as a wrapping material, as well as being a surfactant product that can be washed with.

SUMMARY OF THE INVENTION

In a first aspect, there is provided a solid surfactant cosmetic composition comprising
(i) insoluble vegetable fibre, insoluble fruit fibre or mixture thereof;
(ii) synthetic surfactant; and
(iii) hydrocolloid;
wherein the solid surfactant cosmetic composition is prepared by dehydrating a liquid composition comprising
(i) a vegetable pulp containing insoluble vegetable fibre, a fruit pulp containing insoluble fruit fibre or a mixture thereof, wherein the vegetable pulp, fruit pulp or mixture thereof is in an amount of 55 to 99 wt %;
(ii) synthetic surfactant in an amount of 0.9 to 40 wt. %; and
(iii) hydrocolloid in an amount of 0.1 to 15 wt. %;
wherein the amounts are based on the total combined amount of pulp, synthetic surfactant and hydrocolloid.

In a second aspect, there is provided a solid surfactant cosmetic composition comprising
(i) melon fibre;
(ii) synthetic surfactant; and
(iii) hydrocolloid;
wherein the solid surfactant cosmetic composition is prepared by dehydrating a liquid composition comprising
(i) melon; and
(ii) synthetic surfactant; and
(iii) hydrocolloid.

In a third aspect, there is provided a solid surfactant cosmetic composition comprising
(i) apple fibre;
(ii) synthetic surfactant; and
(iii) hydrocolloid;
wherein the solid surfactant cosmetic composition is prepared by dehydrating a liquid composition comprising
(i) apple pulp; and
(ii) synthetic surfactant; and
(iii) hydrocolloid.

In a fourth aspect, there is provided a solid surfactant cosmetic composition comprising
(i) apple fibre;
(ii) synthetic surfactant; and
(iii) hydrocolloid;
wherein the solid surfactant cosmetic composition is prepared by dehydrating a liquid composition comprising
(i) apple pulp in an amount of 20 to 60 wt. %; and
(ii) synthetic surfactant in an amount of 0.9 to 40 wt. %; and
(iii) hydrocolloid in an amount of 0.1 to 15 wt. %;
wherein the amounts are based on the total amount of the liquid composition.

In a fifth aspect, there is provided a solid surfactant cosmetic composition comprising
(i) insoluble vegetable fibre, insoluble fruit fibre or mixture thereof in an amount of 20 to 85 wt. %;
(ii) synthetic surfactant in an amount of 20 to 75 wt. %; and
(iii) hydrocolloid in an amount of 0.4 to 20 wt. %;
wherein the amounts are based on the total combined amount of fibre, synthetic surfactant and hydrocolloid.

In a sixth aspect, there is provided a process for preparing a solid surfactant cosmetic composition comprising
(i) insoluble vegetable fibre, insoluble fruit fibre or mixture thereof;
(ii) synthetic surfactant; and
(iii) hydrocolloid;
the process comprising the step of
(a) providing a liquid composition comprising
   (i) a vegetable pulp containing insoluble vegetable fibre, a fruit pulp containing insoluble fruit fibre or a mixture thereof, wherein the vegetable pulp, fruit pulp or mixture thereof is in an amount of 55 to 99 wt. %;
   (ii) synthetic surfactant in an amount of 0.9 to 40 wt. %; and
   (iii) hydrocolloid in an amount of 0.1 to 15 wt. %;
   wherein the amounts are based on the total combined amount of pulp, synthetic surfactant and hydrocolloid.
(b) dehydrating the liquid composition to provide the solid surfactant cosmetic composition.

In a seventh aspect, there is provided a product obtained or obtainable by a process in accordance with the present invention.

In an eighth aspect, there is provided a cosmetic method comprising contacting the skin or hair of a user with water into which is dissolved a solid surfactant cosmetic composition of the first, second or third aspect of the invention.

For ease of reference, these and further aspects of the present invention are now discussed under appropriate section headings. However, the teachings under each section are not necessarily limited to each particular section.

Advantages

We found that by providing a solid synthetic surfactant cosmetic composition comprising the specific components of the present invention as described herein, a synthetic surfactant composition is formed having physical characteristics which give a paper like texture. The present invention provides a solid surfactant cosmetic composition which may be used in the form of packaging, which can be used to wrap other products. This wrapping material can be used to protect the products in a wide range of environments, for example in a retail environment. We found that it is then possible to print text and images on to the compositions of the present invention, thus providing a wrapping which, for example, explains the contents of the product within. When the wrapping made from the composition of the present invention has been removed, it can subsequently be used to wash the skin, body or hair. This is highly advantageous because the packaging is used for a further purpose and does not create any solid waste, for example which has to be collected for recycling or which would end up in land fill. This is an exceptional aspect as the creation of excessive packaging is environmentally challenging.

Whilst the primary role of the matrix is to maintain the structural integrity of the solid composition, it has a secondary purpose that allows for the synthetic surfactant to be dispersed throughout its structure. When water permeates the matrix the synthetic surfactant is actuated, allowing the composition to act in the desired manner. The use of a synthetic surfactant, instead of a soap, produces a higher quality finished product, with superior foaming ability and a wider range of uses, such as for washing the body or hair. We have found that by incorporating a hydrocolloid as described herein a pliable sheet may be provided overcoming the problems of prior art sheet products prepared with synthetic surfactants. The present invention provides a form of paper prepared from synthetic surfactant, fibre and hydrocolloid. This forms an excellent paper like texture. It has been surprisingly found that a blend of these ingredients when dehydrated formed a durable material which has the desired properties.

DETAILED DESCRIPTION

Composition

As discussed herein, the present invention provides
a solid surfactant cosmetic composition comprising
(i) insoluble vegetable fibre, insoluble fruit fibre or mixture thereof;
(ii) synthetic surfactant; and
(iii) hydrocolloid;
wherein the solid surfactant cosmetic composition is prepared by dehydrating a liquid composition comprising
(i) a vegetable pulp containing insoluble vegetable fibre, a fruit pulp containing insoluble fruit fibre or mixture thereof, wherein the vegetable pulp, fruit pulp or mixture thereof is in an amount of 55 to 99 wt. %;
(ii) synthetic surfactant in an amount of 0.9 to 40 wt. %; and
(iii) hydrocolloid in an amount of 0.1 to 15 wt. %;
wherein the amounts are based on the total combined amount of pulp, synthetic surfactant and hydrocolloid.
a solid surfactant cosmetic composition comprising
(i) melon fibre;
(ii) synthetic surfactant; and
(iii) hydrocolloid;
wherein the solid surfactant cosmetic composition is prepared by dehydrating a liquid composition comprising
(i) melon; and
(ii) synthetic surfactant; and
(iii) hydrocolloid.
a solid surfactant cosmetic composition comprising
(i) apple fibre;
(ii) synthetic surfactant; and
(iii) hydrocolloid;
wherein the solid surfactant cosmetic composition is prepared by dehydrating a liquid composition comprising
(i) apple pulp; and
(ii) synthetic surfactant; and
(iii) hydrocolloid.
a solid surfactant cosmetic composition comprising
(i) apple fibre;
(ii) synthetic surfactant; and
(iii) hydrocolloid;
wherein the solid surfactant cosmetic composition is prepared by dehydrating a liquid composition comprising
(i) apple pulp in an amount of 20 to 60 wt %;
(ii) synthetic surfactant in an amount of 0.9 to 40 wt. %; and
(iii) hydrocolloid in an amount of 0.1 to 15 wt. %;

wherein the amounts are based on the total amount of the liquid composition.

a solid surfactant cosmetic composition comprising
(i) insoluble vegetable fibre, insoluble fruit fibre or mixture thereof in an amount of 20 to 85 wt. %;
(ii) synthetic surfactant in an amount of 20 to 75 wt. %; and
(iii) hydrocolloid in an amount of 0.4 to 20 wt. %;
wherein the amounts are based on the total combined amount of fibre, synthetic surfactant and hydrocolloid.

The solid products of the present invention are compositions which can substantially sustain their physical shape when unsupported by external means, e.g. packaging etc. Thus, they are considered to be solid, solid like, in solid form or in solid-like form at room temperature. For the avoidance of doubt the solid product must remain substantially solid at up to 30° C.

By solid-like, it is understood that some materials are considered on a day to day basis to be solid, yet over an extremely long period of time, may alter in shape, e.g. amorphous materials such as glass etc. However, they are considered to be solid-like as, for the purpose they fulfil, they are solid.

Due to the solid form of the compositions of the present invention, external packaging is not required to maintain the shape of the composition.

The composition of the present invention is typically provided in the form of a sheet. As will be understood by one skilled in the art, by sheet it is meant a product having thickness of less than 5 mm, such as less than 4 mm, such as less than 2 mm, such as 1 to 2 mm.

Fibre

The solid cosmetic product of the present invention comprises insoluble vegetable fibre, insoluble fruit fibre or mixture thereof. It will be understood by one skilled in the art that by the terms vegetable fibre and fruit fibre it is meant dietary fibre obtained from a vegetable or a fruit, such as a berry. The fibre is will typically be an insoluble dietary fibre. In one aspect the present invention comprises insoluble vegetable fibre. In one aspect the present invention comprises insoluble fruit fibre. In one aspect the present invention comprises insoluble vegetable fibre and insoluble fruit fibre.

As discussed herein, the insoluble vegetable fibre, the insoluble fruit fibre or mixture thereof is prepared by dehydrating a liquid composition comprising a vegetable pulp, a fruit pulp or a mixture thereof. As will be understood by one skilled in the art vegetable pulp or fruit pulp may be obtained by removal, if appropriate, of any skin or seeds and, if required, application of pressure or cutting to the fruit or vegetable. For example, in the case of melon one skilled in the art would prepare pulp by removal of skin and seeds and then mashing or pureeing of the remaining fruit.

As discussed herein, in one aspect the solid surfactant cosmetic composition is prepared by dehydrating a liquid composition comprising a vegetable pulp containing insoluble vegetable fibre, a fruit pulp containing insoluble fruit fibre or a mixture thereof, wherein the vegetable pulp, fruit pulp or mixture thereof is in an amount of 55 to 99 wt. %. In one aspect the solid surfactant cosmetic composition is prepared by dehydrating a liquid composition comprising a vegetable pulp, a fruit pulp or a mixture thereof in an amount of 60 to 95 wt. %, such as in an amount of 60 to 90 wt. %, such as in an amount of 65 to 90 wt. %, such as in an amount of 65 to 85 wt. %, such as in an amount of 67.5 to 85 wt. %, based on the total combined amount of pulp, surfactant and hydrocolloid.

The fibre or pulp may be obtained from any suitable fruit or vegetable. In one aspect the fibre or pulp is obtained from melon, apple, strawberries, mango, pineapple, squashes, potato, sugar beet and mixtures thereof.

In one aspect the fibre or pulp is obtained from melon. The melon which is the source of fibre may be any suitable melon. For example the melon may be of the family Cucumis. In one preferred aspect the melon is of the species *Cucumis melo inodorus*. Preferably the melon is honeydew melon.

In one aspect the solid surfactant cosmetic composition is prepared by dehydrating a liquid composition comprising melon pulp in an amount of 55 to 99 wt. %. In one aspect the solid surfactant cosmetic composition is prepared by dehydrating a liquid composition comprising melon pulp in an amount of 60 to 95 wt. %, such as in an amount of 65 to 95 wt. %, such as in an amount of 70 to 95 wt. %, such as in an amount of 75 to 95 wt. %, such as in an amount of 70 to 90 wt. %, such as in an amount of 70 to 85 wt. %, based on the total combined amount of pulp, surfactant and hydrocolloid. Preferably, the solid surfactant cosmetic composition is prepared by dehydrating a liquid composition comprising melon pulp in an amount of 65 to 85 wt. % based on the total combined amount of pulp, surfactant and hydrocolloid.

In one aspect the solid surfactant cosmetic composition is prepared by dehydrating a liquid composition comprising melon pulp in an amount of 55 to 99 wt. %. In one aspect the solid surfactant cosmetic composition is prepared by dehydrating a liquid composition comprising melon pulp in an amount of 60 to 95 wt. %, such as in an amount of 65 to 95 wt. %, such as in an amount of 65 to 90 wt. %, such as in an amount of 65 to 85 wt. %, such as in an amount of 65 to 80 wt. %, based on the total amount of the liquid composition.

In one aspect the fibre or pulp is obtained from apple. The apple which is the source of the fibre may be any suitable apple.

As will be understood by one skilled in the art, fruit may naturally provide a source of not only insoluble fibre but also sugar. In some aspects of the present invention, pulp is optionally mixed with other components such as sugar and water. In some aspects of the present invention, fruit or vegetable pulp contains all the required components, when mixed with synthetic surfactant and hydrocolloid to provide a composition suitable for dehydration.

We have found that melon provides naturally the desired composition to prepare an effective solid composition for the purposes described herein. Thus in a further aspect the present invention provides a solid surfactant cosmetic composition comprising (i) melon fibre; (ii) synthetic surfactant; and (iii) hydrocolloid; wherein the solid surfactant cosmetic composition is prepared by dehydrating a liquid composition comprising (i) melon; and (ii) synthetic surfactant; and (iii) hydrocolloid.

Typically the (a) melon and (b) synthetic surfactant are combined at a weight ratio of melon to synthetic surfactant of from 19:1 to 3:1, such as from 15:1 to 3:1, such as from 12:1 to 3:1, such as from 10:1 to 3:1, such as from 10:1 to 4:1, such as from 10:1 to 5:1, such as from 10:1 to 6:1, such as from 10:1 to 7:1, such as from 10:1 to 8:1, such as from 10:1 to 9:1, such as from 8:1 to 4:1, such as from 7:1 to 4:1, such as from 6:1 to 4:1, such as from 6:1 to 5:1, such as from 9:1 to 5:1, such as from 7:1 to 5:1, such as from 8:1 to 5:1.

In one aspect (a) honeydew melon and (b) synthetic surfactant are combined at a weight ratio of honeydew melon to synthetic surfactant of from 19:1 to 3:1, such as from 15:1 to 3:1, such as from 12:1 to 3:1, such as from 10:1 to 3:1, such as from 10:1 to 4:1, such as from 10:1 to 5:1, such as from 10:1 to 6:1, such as from 10:1 to 7:1, such as from 10:1 to 8:1, such as from 10:1 to 9:1, such as from 8:1 to 4:1, such as from 7:1 to 4:1, such as from 6:1 to 4:1, such as from 6:1 to 5:1, such as from 9:1 to 5:1, such as from 7:1 to 5:1, such as from 8:1 to 5:1.

We have also found that apple provides naturally the desired composition to prepare an effective solid composition for the purposes described herein. Thus in the third aspect of the present invention, there is provided a solid surfactant cosmetic composition comprising (i) apple fibre; (ii) synthetic surfactant; and (iii) hydrocolloid; wherein the solid surfactant composition is prepared by dehydrating a liquid composition comprising (i) apple pulp; and (ii) synthetic surfactant; and (iii) hydrocolloid.

As the skilled person will appreciate, apple pulp has a high natural insoluble fruit (apple) fibre content and a low natural water content when compared with other vegetable or fruit pulps, such as melon pulp which has a relatively lower insoluble fruit (melon) fibre content and a relatively higher natural water content. Therefore, we have found that dehydrating a liquid composition comprising a lower amount of apple pulp may result in the production of a solid surfactant cosmetic composition suitable for the purposes described herein since the apple pulp contains a higher proportion of insoluble fruit fibre.

Therefore, in the fourth aspect of the present invention, there is provided a solid surfactant cosmetic composition comprising (i) apple fibre; (ii) synthetic surfactant; and (iii) hydrocolloid; wherein the solid surfactant cosmetic composition is prepared by dehydrating a liquid composition comprising (i) apple pulp in an amount of 20 to 60 wt. %; and (ii) synthetic surfactant in an amount of 0.9 to 40 wt. %; and (iii) hydrocolloid in an amount of 0.1 to 15 wt. %; wherein the amounts are based on the total amount of the liquid composition.

As discussed herein, in one aspect the solid surfactant cosmetic composition is prepared by dehydrating a liquid composition comprising apple pulp containing insoluble apple fibre, wherein the apple pulp is in an amount of 20 to 60 wt. %. In one aspect the solid surfactant cosmetic composition is prepared by dehydrating a liquid composition comprising apple pulp in an amount of 25 to 55 wt. %, such as in an amount of 25 to 50 wt. %, such as in an amount of 30 to 45 wt. %, such as in an amount of 30 to 40 wt. %, based on the total amount of the liquid composition.

In the product of the fifth aspect of the present invention, the solid surfactant cosmetic composition comprises vegetable fibre, fruit fibre or mixture thereof, in an amount of 20 to 85 wt. % based on the total combined amount of the fibre, surfactant and hydrocolloid, such as in an amount of 25 to 80 wt. % based on the total combined amount of the fibre, surfactant and hydrocolloid, such as in an amount of 30 to 75 wt. % based on the total combined amount of the fibre, surfactant and hydrocolloid, such as in an amount of 35 to 70 wt. % based on the total combined amount of the fibre, surfactant and hydrocolloid.

In the product of the fifth aspect of the present invention, the solid surfactant cosmetic composition comprises vegetable fibre, fruit fibre or mixture thereof, in an amount of 20 to 75 wt. % based on the total amount of the solid cosmetic surfactant composition, such as in an amount of 20 to 70 wt. % based on the total amount of the solid surfactant cosmetic composition, such as in an amount of 20 to 65 wt. % based on the total amount of the solid surfactant cosmetic composition, such as in an amount of 25 to 65 wt. % based on the total amount of the solid surfactant cosmetic composition, such as in an amount of 30 to 65 wt. % based on the total amount of the solid surfactant cosmetic composition, such as in an amount of 35 to 65 wt. % based on the total amount of the solid surfactant cosmetic composition.

The solid cosmetic composition is preferably prepared by dehydrating a liquid composition comprising a vegetable fibre, a fruit fibre or mixture thereof, in an amount of 1 to 40 wt. % based on the total amount of the liquid composition, such as in an amount of 5 to 35 wt. % based on the total amount of the liquid composition, such as in an amount of 10 to 34 wt. % based on the total amount of the liquid composition.

Synthetic Surfactant

The solid cosmetic product of the present invention comprises a synthetic surfactant. It will be understood by one skilled in the art that by the term synthetic surfactant it is meant a surfactant that is not a soap i.e. a surfactant that is not a salt of a fatty acid.

In one aspect the synthetic surfactant is selected from cationic surfactants, non-ionic surfactants, amphoteric surfactants, alkylbenzene sulfonate surfactants, alkyl sulphate surfactants, alkyl ether sulphate surfactants and mixtures thereof.

In one aspect the synthetic surfactant is selected from sodium lauryl sulphate, sodium cocoamphoacetate, sodium laureth sulphate, lauryl betaine, sodium lauroyl sarcosinate, sodium alkyl sulphate, disodium lauryl sulfosuccinate, disodium laureth sulfosuccinate, cocamide monoethanolamine, cetrimonium bromide, sodium and mixtures thereof. In one aspect the synthetic surfactant is sodium lauryl sulphate.

In one aspect the synthetic surfactant is anhydrous. In one aspect the synthetic surfactant is anhydrous sodium lauryl sulphate.

The solid cosmetic composition is preferably prepared by dehydrating a liquid composition comprising synthetic surfactant in an amount of 5 to 35 wt. % based on the total combined amount of the pulp, surfactant and hydrocolloid, such as in an amount of 5 to 30 wt. % based on the total combined amount of the pulp, surfactant and hydrocolloid, such as in an amount of 10 to 30 wt. % based on the total combined amount of the pulp, surfactant and hydrocolloid, such as in an amount of 15 to 30 wt. % based on the total combined amount of the pulp, surfactant and hydrocolloid, such as in an amount of 20 to 30 wt. % based on the total combined amount of the pulp, surfactant and hydrocolloid.

The solid cosmetic composition is preferably prepared by dehydrating a liquid composition comprising synthetic surfactant in an amount of 5 to 35 wt. % based on the total amount of the liquid composition, such as in an amount of 5 to 30 wt. % based on the total amount of liquid composition, such as in an amount of 10 to 30 wt. % based on the total amount of the liquid composition, such as in an amount of 10 to 25 wt. % based on the total amount of the liquid composition, such as in an amount of 10 to 20 wt. % based on the total amount of the liquid composition.

In the product of the fifth aspect of the present invention, the solid cosmetic composition comprises synthetic surfactant in an amount of 20 to 75 wt. % based on the total combined amount of the fibre, surfactant and hydrocolloid, such as in an amount of 20 to 70 wt. % based on the total combined amount of the fibre, surfactant and hydrocolloid, such as in an amount of 25 to 65 wt. % based on the total combined amount of the fibre, surfactant and hydrocolloid, such as in an amount of 25 to 60 wt. % based on the total combined amount of the fibre, surfactant and hydrocolloid, such as in an amount of 25 to 55 wt. % based on the total combined amount of the fibre, surfactant and hydrocolloid, such as in an amount of 25 to 50 wt. % based on the total combined amount of the fibre, surfactant and hydrocolloid, such as in an amount of 25 to 47.5 wt. % based on the total combined amount of the fibre, surfactant and hydrocolloid.

In the product of the fifth aspect of the present invention, the solid cosmetic composition comprises synthetic surfactant in an amount of 20 to 75 wt. % based on the total amount of the solid surfactant cosmetic composition, such as in an amount of 20 to 70 wt. % based on the total amount of the solid surfactant cosmetic composition, such as in an amount of 20 to 65 wt. % based on the total amount of the solid surfactant cosmetic composition, such as in an amount of 20 to 60 wt. % based on the total amount of the solid surfactant cosmetic composition, such as in an amount of 20 to 55 wt. % based on the total amount of the solid surfactant cosmetic composition, such as in an amount of 20 to 50 wt. % based on the total amount of the solid surfactant cosmetic composition, such as in an amount of 20 to 45 wt. % based on the total amount of the solid surfactant cosmetic composition, such as in an amount of 20 to 40 wt. % based on the total amount of the solid surfactant cosmetic composition, such as in an amount of 22.5 to 37.5 wt. % based on the total amount of the solid surfactant cosmetic composition.

Hydrocolloid

The solid cosmetic product of the present invention comprises a hydrocolloid. The hydrocolloid may be selected from any suitable hydrocolloids In one aspect the hydrocolloid is selected from cellulose, cellulose derivatives (such as ethylcellulose, hydroxypropylmethylcellulose, methylcellulose, hydroxyethylcellulose, hydroxypropylcellulose, sodium carboxymethylcellulose, carboxymethylcellulose, calcium carboxymethylcellulose), alginate, pectin, xanthan, tragacanth and mixtures thereof. In one aspect the hydrocolloid is selected from cellulose, hydroxypropylcellulose, alginate, pectin, xanthan, tragacanth and mixtures thereof. In one aspect the hydrocolloid is selected from cellulose, hydroxypropylcellulose, alginate, and mixtures thereof. In one aspect the hydrocolloid is selected from cellulose, hydroxypropylcellulose, and mixtures thereof. In one aspect the hydrocolloid is cellulose. In one aspect the hydrocolloid is hydroxypropylcellulose.

As discussed herein the solid surfactant cosmetic composition may be prepared by dehydrating a liquid composition comprising hydrocolloid in an amount of 0.1 to 15 wt. %; based on the total combined amount of pulp, surfactant and hydrocolloid. The solid cosmetic composition is preferably prepared by dehydrating a liquid composition comprising hydrocolloid in an amount of 0.1 to 12 wt. % based on the total combined amount of the pulp, surfactant and hydrocolloid, such as in an amount of 0.1 to 10 wt. % based on the total combined amount of the pulp, surfactant and hydrocolloid, such as in an amount of 0.1 to 9 wt. % based on the total combined amount of the pulp, surfactant and hydrocolloid, such as in an amount of 0.2 to 9 wt. % based on the total combined amount of the pulp, surfactant and hydrocolloid, such as in an amount of 0.3 to 9 wt. % based on the total combined amount of the pulp, surfactant and hydrocolloid, such as in an amount of 0.4 to 9 wt. % based on the total combined amount of the pulp, surfactant and hydrocolloid, such as in an amount of 0.5 to 8.5 wt. % based on the total combined amount of the pulp, surfactant and hydrocolloid. The solid cosmetic composition is preferably prepared by dehydrating a liquid composition comprising hydrocolloid in an amount of 0.5 to 10 wt. % based on the total combined amount of the pulp, surfactant and hydrocolloid.

In one aspect the solid surfactant cosmetic composition may be prepared by dehydrating a liquid composition comprising hydrocolloid in an amount of 0.1 to 15 wt. %; based on the total amount of liquid composition. The solid cosmetic composition is preferably prepared by dehydrating a liquid composition comprising hydrocolloid in an amount of 0.1 to 12 wt % based on the total amount of the liquid composition, such as in an amount of 0.1 to 10 wt. % based on the total amount of the liquid composition, such as in an amount of 0.1 to 8 wt. % based on the total amount of the liquid composition, such as in an amount of 0.1 to 6 wt. % based on the total amount of the liquid composition, such as in an amount of 0.1 to 5 wt. % based on the total amount of the liquid composition, such as in an amount of 0.1 to 4.5 wt. % based on the total amount of the liquid composition, such as in an amount of 0.25 to 4.5 wt. % based on the total amount of the liquid composition, such as in an amount of 0.4 to 5 wt % based on the total amount of the liquid composition, such as in an amount of 0.45 to 4.5 wt. % based on the total amount of the liquid composition.

In the product of the fifth aspect of the present invention, the solid cosmetic composition comprises hydrocolloid in an amount of 0.4 to 20 wt. % based on the total combined amount of the fibre, surfactant and hydrocolloid, such as in an amount of 0.4 to 20 wt. % based on the total combined amount of the fibre, surfactant and hydrocolloid, such as in an amount of 0.4 to 17.5 wt. % based on the total combined amount of the fibre, surfactant and hydrocolloid, such as in an amount of 0.4 to 17 wt. % based on the total combined amount of the fibre, surfactant and hydrocolloid, such as in an amount of 0.5 to 17 wt. % based on the total combined amount of the fibre, surfactant and hydrocolloid, such as in an amount of 1 to 17 M. % based on the total combined amount of the fibre, surfactant and hydrocolloid, such as in an amount of 2 to 17 wt. % based on the total combined amount of the fibre, surfactant and hydrocolloid, such as in an amount of 3 to 17 wt. % based on the total combined amount of the fibre, surfactant and hydrocolloid.

In the product of the fifth aspect of the present invention, the solid cosmetic composition comprises hydrocolloid in an amount of 0.4 to 20 wt. % based on the total amount of the solid surfactant cosmetic composition, such as in an amount of 0.4 to 15 wt. % based on the total amount of the solid surfactant cosmetic composition, such as in an amount of 0.4 to 12 wt. % based on the total amount of the solid surfactant cosmetic composition, such as in an amount of 0.5 to 12 wt. % based on the total amount of the solid surfactant cosmetic composition, such as in an amount of 0.6 to 12 wt. % based on the total amount of the solid surfactant cosmetic composition, such as in an amount of 1 to 12 wt. % based on the total amount of the solid surfactant cosmetic composition, such as in an amount of 2 to 12 wt. % based on the total amount of the solid surfactant cosmetic composition, such as in an amount of 3 to 12 wt. % based on the total amount of the solid surfactant cosmetic composition.

Sugar

As discussed herein, in one aspect the surfactant product of the present invention may comprise sugar. A sugar as described herein is a mono-saccharide or a disaccharide. Thus references herein to sugar may be read to mean mono-saccharides, disaccharides or mixtures thereof. In one aspect the sugar is selected from mono-saccharides. In one aspect the sugar is selected from di-saccharides.

The solid cosmetic composition is preferably prepared by dehydrating a liquid composition comprising sugar in an amount of 2 to 35 wt. % based on the total combined amount of the pulp, surfactant, hydrocolloid and sugar, such as in an amount of 2 to 30 wt. % based on the total combined amount of the pulp, surfactant, hydrocolloid and sugar, such as in an amount of 2 to 25 wt. % based on the total combined amount of the pulp, surfactant, hydrocolloid and sugar, such as in an amount of 2 to 20 wt. % based on the total combined amount of the pulp, surfactant, hydrocolloid and sugar, such as in an amount of 2 to 15 wt. % based on the total combined amount of the pulp, surfactant, hydrocolloid and sugar, such as in an amount of 2 to 13 wt. % based on the total combined amount of the pulp, surfactant, hydrocolloid and sugar, such as in an amount of 2 to 12 wt. % based on the total combined amount of the pulp, surfactant, hydrocolloid and sugar, such as in an amount of 2 to 11 wt % based on the total combined amount of the pulp, surfactant, hydrocolloid and sugar, such as in an amount of 4 to 11 wt. % based on the total combined amount of the pulp, surfactant, hydrocolloid and sugar, such as in an amount of 6 to 11 wt. % based on the total combined amount of the pulp, surfactant, hydrocolloid and sugar, such as in an amount of 6 to 9 wt % based on the total combined amount of the pulp, surfactant, hydrocolloid and sugar.

In a preferred product to be dehydrated, the sugar is present in an amount of 6.75 to 8.6 wt. % based on the total combined amount of the pulp, surfactant, hydrocolloid and sugar. In one aspect the solid cosmetic composition is preferably prepared by dehydrating a liquid composition comprising sugar in an amount of 7.1 to 8.6 wt. % based on the total combined amount of the pulp, surfactant, hydrocolloid and sugar such as in an amount of 7.6 to 8.6 wt. % based on the total combined amount of the pulp, surfactant, hydrocolloid and sugar, such as in an amount of 7.8 to 8.4 wt. % based on the total combined amount of the pulp, surfactant, hydrocolloid and sugar, such as in an amount of 7.9 to 8.3 wt. % based on the total combined amount of the pulp, surfactant, hydrocolloid and sugar, such as in an amount of approximately 8.1 wt. % based on the total combined amount of the pulp, surfactant, hydrocolloid and sugar, such as in an amount of 7.1 to 8.1 wt. % based on the total combined amount of the pulp, surfactant, hydrocolloid and sugar, such as in an amount of 7.4 to 7.9 wt. % based on the total combined amount of the pulp, surfactant, hydrocolloid and sugar, such as in an amount of approximately 7.65 wt. % based on the total combined amount of the pulp, surfactant, hydrocolloid and sugar.

Water

The solid cosmetic composition of the first aspect may be prepared by dehydrating a liquid composition comprising water in an amount of 30 to 85 M. % based on the total combined amount of the fibre, surfactant, hydrocolloid and water. Preferably the solid cosmetic composition is prepared by dehydrating a liquid composition comprising water in an amount of 30 to 80 wt. % based on the total combined amount of the fibre, surfactant, hydrocolloid and water, such as in an amount of 35 to 75 wt. % based on the total combined amount of the fibre, surfactant, hydrocolloid and water, such as in an amount of 40 to 75 wt. % based on the total combined amount of the fibre, surfactant, hydrocolloid and water.

The solid cosmetic composition of the third aspect (comprising apple fibre) may be prepared by dehydrating a liquid composition comprising water in an amount of 30 to 60 wt. % based on the total combined amount of the pulp, surfactant, hydrocolloid and water. In other words, the solid cosmetic composition of the third aspect (comprising apple fibre) may be prepared by dehydrating a liquid composition which includes 30 to 60 wt. % water in addition to the water contained in the apple pulp itself. Preferably the solid cosmetic composition is prepared by dehydrating a liquid composition comprising water in an amount of 30 to 55 wt. % based on the total combined amount of the pulp, surfactant, hydrocolloid and water, such as in an amount of 35 to 55 wt. % based on the total combined amount of the pulp, surfactant, hydrocolloid and water, such as in an amount of 40 to 55 wt. % based on the total combined amount of the pulp, surfactant, hydrocolloid and water.

The solid cosmetic composition of the third aspect (comprising apple fibre) may be prepared by dehydrating a liquid composition comprising water in an amount of 45 to 85 wt. % based on the total combined amount of the fibre, surfactant, hydrocolloid and water. Preferably the solid cosmetic composition is prepared by dehydrating a liquid composition comprising water in an amount of 45 to 80 wt. % based on the total combined amount of the fibre, surfactant, hydrocolloid and water, such as in an amount of 45 to 75 wt. % based on the total combined amount of the fibre, surfactant, hydrocolloid and water, such as in an amount of 50 to 75 wt. % based on the total combined amount of the fibre, surfactant, hydrocolloid and water.

In the product of the fifth aspect of the present invention, the solid cosmetic composition may comprise water in an amount of 1 to 30 wt. % based on the total combined amount of the fibre, surfactant, hydrocolloid and water, such as in an amount of 1 to 25 wt. % based on the total combined amount of the fibre, surfactant, hydrocolloid and water, such as in an amount of 1 to 20 wt. % based on the total combined amount of the fibre, surfactant, hydrocolloid and water, such as in an amount of 1 to 15 wt. % based on the total combined amount of the fibre, surfactant, hydrocolloid and water, such as in an amount of 1 to 10 wt. % based on the total combined amount of the fibre, surfactant, hydrocolloid and water, such as in an amount of 1 to 7 wt. % based on the total combined amount of the fibre, surfactant, hydrocolloid and water, such as in an amount of 3 to 7 wt. % based on the total combined amount of the fibre, surfactant, hydrocolloid and water.

Thickener

In one preferred aspect the solid cosmetic composition further comprises a thickener. Preferably this is selected from cosmetically acceptable clays, starch, acrylic acid polymers and salts thereof, and mixtures thereof. In one aspect, the thickener is selected from cosmetically acceptable clays. Preferably the thickener is selected from kaolin, calamine, smectite clay and mixtures thereof. In one aspect, the thickener is starch. Preferably, the thickener is selected from corn starch, potato starch, tapioca starch, rice starch and mixtures thereof. In one aspect, the thickener is acrylic acid polymers and salts thereof.

Preferably, the thickener is sodium polyacrylate.

It will be appreciated by one skilled in the art that the thickener may be present in any suitable amount to provide the desired solid cosmetic composition. For example the thickener may be present in an amount of 1 to 50 wt. % based on the total weight of the solid composition, such as present in an amount of 1.5 to 25 wt. % based on the total weight of the solid composition, such as present in an amount of 1.7 to 20 wt. % based on the total weight of the solid composition, such as present in an amount of 1.9 to 15 wt. % based on the total weight of the solid composition. The solid cosmetic composition may be prepared by dehydrating a liquid composition comprising thickener in an amount of 1 to 20 wt. % based on the total weight of the liquid composition, such as in an amount of 1 to 15 wt. % based on the total weight of the liquid composition, such as in an amount of 1 to 12 wt. % based on the total weight of the liquid composition, such as in an amount of 1 to 10 wt. % based on the total weight of the liquid composition.

Process

As discussed herein, the invention provides a process for preparing a solid surfactant cosmetic composition comprising
(i) insoluble vegetable fibre, insoluble fruit fibre or mixture thereof;
(ii) synthetic surfactant; and
(iii) hydrocolloid;
the process comprising the step of
(a) providing a liquid composition comprising
   (i) a vegetable pulp containing insoluble vegetable fibre, a fruit pulp containing insoluble fruit fibre or a mixture thereof in an amount of 55 to 99 wt. %;
   (ii) synthetic surfactant in an amount of 0.9 to 40 wt. %; and
   (iii) hydrocolloid in an amount of 0.1 to 15 wt. %;
   wherein the amounts are based on the total combined amount of pulp, surfactant and hydrocolloid, and
(b) dehydrating the liquid composition to provide the solid surfactant cosmetic composition.

Preferably the liquid composition is provided by mixing
(i) melon; and
(ii) synthetic surfactant; and
(iii) hydrocolloid.

Thus in one aspect the present invention provides a process for preparing a solid cosmetic composition comprising (i) melon fibre; (ii) synthetic surfactant; and (iii) hydrocolloid; the process comprising the steps of
(a) providing a liquid composition comprising (i) melon; (ii) synthetic surfactant; and (iii) hydrocolloid,
(b) dehydrating the liquid composition to provide the solid cosmetic composition.

In a further aspect the present invention provides a process for preparing a solid cosmetic composition comprising (i) honeydew melon fibre; (ii) synthetic surfactant; and (iii) hydrocolloid; the process comprising the steps of
(a) providing a liquid composition comprising (i) honeydew melon; (ii) synthetic surfactant; and (iii) hydrocolloid,
(b) dehydrating the liquid composition to provide the solid cosmetic composition.

In a further aspect the present invention provides a process for preparing a solid cosmetic composition comprising (i) apple fibre; (ii) synthetic surfactant; and (iii) hydrocolloid; the process comprising the steps of
(a) providing a liquid composition comprising (i) apple pulp; (ii) synthetic surfactant; and (iii) hydrocolloid,
(b) dehydrating the liquid composition to provide the solid cosmetic composition.

In a further aspect the present invention provides a process for preparing a solid cosmetic composition comprising (i) apple fibre; (ii) synthetic surfactant; and (iii) hydrocolloid; the process comprising the steps of
(a) providing a liquid composition comprising
   (i) apple pulp in an amount of 20 to 60 wt. %;
   (ii) synthetic surfactant in an amount of 0.9 to 40 wt. %; and
   (iii) hydrocolloid in an amount of 0.1 to 15 wt. %;
   wherein the amounts are based on the total combined amount of pulp, surfactant and hydrocolloid, and
(b) dehydrating the liquid composition to provide the solid cosmetic composition.

The shape of the solid products of the present invention is not limited. However, they are typically dehydrated in the form of a sheet. However, it is envisaged that they may be produced in the form from which sheets may be cut or sliced.

As described herein, the solid product may further comprise one or more cosmetically acceptable additives. In one embodiment, the process further comprises the step of combining with the liquid composition, one or more cosmetically acceptable additives as defined herein.

The liquid composition is dehydrated to provide the solid cosmetic composition using any suitable dehydrating technique. In a typical technique the liquid composition is poured on to a flat sheet. Preferably the liquid is poured to a depth of half a centimeter thick. The liquid product may then be placed in a de-hydrating oven, for example at a temperature of 55° C. for between 8 to 15 hours. This time and temperature may be varied depending on the liquid composition.

In one aspect the process further comprised the step of printing an image or applying ink on the solid surfactant cosmetic composition. The image may be printed or the ink applied by spraying, painting or rolling.

The present invention also provides a product obtained or obtainable by a process described herein.

Additional Components

The solid product of the present invention may also comprise one or more cosmetically acceptable additives. The person skilled in the art is aware of a range of cosmetically acceptable additives which are suitable for incorporation into such compositions. For example, binders, fillers, opacifiers, perfumes, colours, fragrances, decorative items, herbs and mixtures thereof. Preferably the solid cosmetic composition comprises at least one additional component selected from colours, fragrances, herbs and mixtures thereof.

The combined amount of cosmetically acceptable additives is preferably from about 0.1% to about 20% by weight of the total solid composition, such as from about 0.1% to about 10% by weight of the total solid composition, such as from about 1% to about 10% by weight of the total solid composition, such as from about 2% to about 10% by weight of the total solid composition, such as from about 4% to about 10% by weight of the total solid composition, such as from about 4% to about 8% by weight of the total solid composition, such as from about 5% to about 7% by weight of the total solid composition.

The combined amount of colours and fragrances is preferably from about 0.1% to about 10% by weight of the total solid composition, such as from about 0.1% to about 5% by weight of the total solid composition, such as from about 0.5% to about 5% by weight of the total solid composition, such as from about 1% to about 5% by weight of the total solid composition, such as from about 1% to about 4% by weight of the total solid composition, such as from about 1% to about 3% by weight of the total solid composition, such as from about 1% to about 2% by weight of the total solid composition.

Fruit and herb extracts and juices, vegetable oils and essential oils are all compatible with the solid composition. Colours, both naturally derived and synthetic can be used to colour the product. Cosmetic colour is added to the invention to form bright colourful shapes and bars of the mixture. This colour can be a blend of synthetic cosmetic pigments, such as FD&C Blue No1, FD&C Red No 4 and others. Also naturally derived colours such as gardenia extract or chlorophyll extract.

The amount of colour is preferably from about 0.01% to about 10% by weight of the total solid composition, such as from about 0.01% to about 5% by weight of the total solid composition, such as from about 0.01% to about 4% by weight of the total solid composition, such as from about 0.01% to about 3% by weight of the total solid composition, such as from about 0.01% to about 2% by weight of the total solid composition, such as from about 0.02% to about 2% by weight of the total solid composition, such as from about 0.05% to about 2% by weight of the total solid composition, such as from about 0.1% to about 2% by weight of the total solid composition, such as from about 0.2% to about 2% by weight of the total solid composition, such as from about 0.2% to about 1% by weight of the total solid composition, such as from about 0.2% to about 0.8% by weight of the total solid composition, such as from about 0.2% to about 0.6% by weight of the total solid composition, such as from about 0.4% to about 0.6% by weight of the total solid composition.

In one embodiment, the cosmetically acceptable additives are selected from the group consisting of essential oils, vitamins, fragrances, colourings, clays, decorative articles, herbs and mixtures thereof.

The amount of herbs is preferably from about 0.1% to about 10% by weight of the total solid composition, such as from about 1% to about 10% by weight of the total solid composition, such as from about 1% to about 8% by weight of the total solid composition, such as from about 2% to about 8% by weight of the total solid composition, such as from about 3% to about 7% by weight of the total solid composition, such as from about 4% to about 6% by weight of the total solid composition.

Fragrance may be added to the product to make the experience of using the present composition more pleasant. Combining essential oils such as lavender, chamomile or rose absolute into fragrances for the invention ensures the user has a pleasant washing experience.

The amount of fragrances is preferably from about 0.1% to about 10% by weight of the total solid composition, such as from about 0.1% to about 5% by weight of the total solid composition, such as from about 0.1% to about 4% by weight of the total solid composition, such as from about 0.5% to about 5% by weight of the total solid composition, such as from about 1% to about 5% by weight of the total solid composition, such as from about 0.5% to about 4% by weight of the total solid composition, such as from about 0.5% to about 3% by weight of the total solid composition, such as from about 0.5% to about 2% by weight of the total solid composition, such as from about 0.5% to about 1.5% by weight of the total solid composition.

The essential oils may be selected based on the fragrance desired, skin type to be treated and other effects desired based on the known properties of essential oils. The addition of essential oils, when taken in to the nose, are known to alter mood. For example, essential oils are known to create effects of drowsiness or stimulating the senses. Many well documented effects can be achieved by the use of essential oils.

In one embodiment, the one or more essential oils present in the solid product are selected from Tarragon, Lemon myrtle, Jasmin, Ylang ylang, Labdanum, Lemongrass, Rose otto, Grapefruit, Patchouli, Rosemary, Armois, Lemon, Neroli, Sweet violet, Lavender, Orange 50 fold, Vanilla, Peppermint, Benzoin, Hydrangia, *Litsea Cubeba*, Cardamon, Tonka, and Chamomile blue. In one embodiment, the one or more essential oils present in the solid product are selected from Tarragon, Lemon myrtle, Labdunum, and Lemon.

Vitamins, particularly B, C and E are very beneficial for the skin. Vitamin rich ingredients such as Wheatgerm oil can also be used to deliver vitamins on to the skin. In a one embodiment, the vitamins are selected from vitamin B, vitamin C, vitamin E and mixtures thereof. It will be appreciated by one skilled in the art that the vitamin may be provided from any suitable source. For example the vitamin(s) may be provided from a synthetic source or from incorporation into the solid product of a material, such as a natural material, that has a high vitamin content.

The ingredients of the present invention do not require cosmetic preservatives. The use of cosmetic preservatives can increase the potential to irritate the skin.

The above ranges provide preferred amounts of each of the components. Each of these ranges may be taken alone or combined with one or more other component ranges to provide a preferred aspect of the invention.

Method

In one aspect of the present invention, there is provided a method comprising contacting the skin or hair of a user with water in which the solid product as defined herein has dissolved or in which the solid product as defined herein is dissolving.

EXAMPLES

The invention will now be described with reference to the following non-limiting examples.

Example 1

A liquid composition having the following composition was prepared.

| Raw Material Type | Batch Size - 2000.00 g | Formula wt. % |
| --- | --- | --- |
| Melon Pulp Honeydew - Fresh | 1598.00 | 79.90 |
| Sodium Lauryl Sulphate - Needles | 300.00 | 15.00 |
| Water - Tap | 1.80 | 0.09 |
| CI42090 FD&C Blue No 1 | 0.20 | 0.01 |
| Cellulose | 40.00 | 2.00 |
| Fragrance | 60.00 | 3.00 |
|  | 2000.00 | 100.00 |

The composition was prepared and dehydrated as follows:
1. Chop up the melon, discarding the seeds and skin, and blend to a smooth puree.
2. Warm the melon pulp to 60° C. and add the SLS and cellulose. Blend the resulting mixture to dissolve all the component parts.
3. Add the fragrance and other components, followed by stirring to disperse the various ingredients.
4. Pour onto a suitable tray to an even thickness of 5 mm.
5. Dry the resulting composition for approximately 9 hours at 55° C. until sufficiently dry enough to remove from the tray.

The dehydration of the mixture evaporated the major part of the water content. This left the fruit fibres and the synthetic surfactant to form structure. The solid composition was approximately one third of the weight of the liquid composition from which it was prepared. The solid composition was prepared having the following composition:

| Raw Material Type | Batch Size - 2000.00 g | Formula wt. % |
| --- | --- | --- |
| Melon Fibre Honeydew - Fresh | 1177.40 | 58.87 |
| Sodium Lauryl Sulphate - Needles | 523.29 | 26.16 |
| Water - Tap | 90.00 | 4.50 |

-continued

| Raw Material Type | Batch Size - 2000.00 g | Formula wt. % |
|---|---|---|
| CI42090 FD&C Blue No 1 | 34.89 | 1.74 |
| Cellulose | 69.77 | 3.49 |
| Fragrance | 104.65 | 5.23 |
|  | 2000.00 | 100.00 |

The dehydrated product was a sheet product that was pliable and foldable.

Example 2

A liquid composition having the following composition was prepared.

| Raw Material Type | Batch Size - 2000.00 g | Formula wt. % |
|---|---|---|
| Melon Pulp Honeydew - Fresh | 1324.20 | 66.21 |
| Sodium Lauryl Sulphate - Needles | 270.00 | 13.50 |
| Smectite Clay | 200.00 | 10.00 |
| Granulated Sugar | 134.80 | 6.74 |
| Water - Tap | 1.80 | 0.09 |
| CI42090 FD&C Blue No 1 | 0.20 | 0.01 |
| Cellulose | 9.00 | 0.45 |
| Fragrance | 60.00 | 3.00 |
|  | 2000.00 | 100.00 |

The composition was prepared in accordance with the method of Example 1.

The dehydration of the mixture evaporated the major part of the water content. This left the fruit fibres and the synthetic surfactant to form structure. The solid composition was approximately one third of the weight of the liquid composition from which it was prepared. The solid composition was prepared having the following composition:

| Raw Material Type | Batch Size - 2000.00 g | Formula wt. % |
|---|---|---|
| Melon Fibre Honeydew - Fresh | 930.20 | 46.51 |
| Sodium Lauryl Sulphate - Needles | 401.85 | 20.09 |
| Smectite Clay | 297.66 | 14.88 |
| Granulated Sugar | 200.62 | 10.03 |
| Water - Tap | 64.00 | 3.20 |
| CI42090 FD&C Blue No 1 | 2.98 | 0.15 |
| Cellulose | 13.39 | 0.68 |
| Fragrance | 89.30 | 4.46 |
|  | 2000.00 | 100.00 |

The dehydrated product was a sheet product that was pliable and foldable.

Example 3

A liquid composition having the following composition was prepared.

| Raw Material Type | Batch Size - 1000.00 g | Formula wt. % |
|---|---|---|
| Apple Pulp (Braeburn) - Fresh | 399.50 | 39.95 |
| Water - Tap | 399.50 | 39.95 |
| Sodium Lauryl Sulphate - Needles | 140.00 | 14.00 |
| Hydroxypropyl methylcellulose | 20.00 | 2.00 |
| Sodium Polyacrylate | 10.00 | 1.00 |
| FD&C Yellow No 5 - 10% solution | 1.00 | 0.10 |
| Fragrance | 30.00 | 3.00 |
|  | 1000.00 | 100.00 |

The composition was prepared and dehydrated as follows:
1. The apple was chopped, discarding the seeds and skin, and blended to a smooth puree.
2. The SLS, cellulose derivative and sodium polyacrylate were added at room temperature. The resulting mixture was blended to dissolve all the component parts.
3. The fragrance and other components were added, followed by stirring to disperse the various ingredients.
4. The liquid composition was poured onto a suitable tray to an even thickness of 5 mm.
5. The resulting composition was dried for approximately 6 hours at 35° C. until sufficiently dry enough to remove from the tray.

The dehydration of the mixture evaporated the major part of the water content. This left the fruit fibres and the synthetic surfactant to form structure. The solid composition was approximately one third of the weight of the liquid composition from which it was prepared. The solid composition was prepared having the following composition:

| Raw Material Type | Batch Size - 1000.00 g | Formula wt. % |
|---|---|---|
| Apple Fibre (Braeburn) - Fresh | 439.40 | 43.94 |
| Water - Tap | 38.00 | 3.80 |
| Sodium Lauryl Sulphate - Needles | 364.00 | 36.40 |
| Hydroxylpropyl methylcellulose | 52.00 | 5.20 |
| Sodium Polyacrylate | 26.00 | 2.60 |
| FD&C Yellow No 5 - 10% solution | 2.60 | 0.26 |
| Fragrance | 78.00 | 7.80 |
|  | 1000.00 | 100.00 |

The dehydrated product was a sheet product that was pliable and foldable.

Example 4

A liquid composition having the following composition was prepared.

| Raw Material Type | Batch Size - 1000.00 g | Formula wt. % |
|---|---|---|
| Apple Pulp (Braeburn) - Fresh | 310.00 | 31.00 |
| Water - Tap | 505.00 | 50.50 |
| Sodium Lauryl Sulphate - Needles | 118.00 | 11.80 |
| FD&C Yellow No 5 - 10% solution | 2.00 | 0.20 |

-continued

| Raw Material Type | Batch Size - 1000.00 g | Formula wt. % |
|---|---|---|
| Fragrance | 15.00 | 1.50 |
| Corn Starch | 22.50 | 2.25 |
| Cellulose | 27.50 | 2.75 |
| | 1000.00 | 100.00 |

The composition was prepared in accordance with the method of Example 3.

The dehydration of the mixture evaporated the major part of the water content. This left the fruit fibres and the synthetic surfactant to form structure. The solid composition was approximately one third of the weight of the liquid composition from which it was prepared. The solid composition was prepared having the following composition:

| Raw Material Type | Batch Size - 1000.00 g | Formula wt. % |
|---|---|---|
| Apple Fibre (Braeburn) - Fresh | 362.25 | 36.23 |
| Water - Tap | 55.00 | 5.50 |
| Sodium Lauryl Sulphate - Needles | 371.70 | 37.17 |
| FD&C Yellow No 5 - 10% solution | 6.30 | 0.63 |
| Fragrance | 47.24 | 4.72 |
| Corn Starch | 70.88 | 7.09 |
| Cellulose | 86.63 | 8.66 |
| | 1000.00 | 100.00 |

The dehydrated product was a sheet product that was pliable and foldable.

Example 5

A liquid composition having the following composition was prepared.

| Raw Material Type | Batch Size - 1000.00 g | Formula wt. % |
|---|---|---|
| Apple Pulp (Braeburn) - Fresh | 357.50 | 35.75 |
| Water - Tap | 392.50 | 39.25 |
| Sodium Lauryl Sulphate - Needles | 122.00 | 12.20 |
| Granulated Sugar | 40.00 | 4.00 |
| FD&C Yellow No 5 - 10% solution | 8.00 | 0.80 |
| Fragrance | 15.00 | 1.50 |
| Smectite Clay | 22.50 | 2.25 |
| Cellulose | 42.50 | 4.25 |
| | 1000.00 | 100.00 |

The composition was prepared in accordance with the method of Example 3.

The dehydration of the mixture evaporated the major part of the water content. This left the fruit fibres and the synthetic surfactant to form structure. The solid composition was approximately one third of the weight of the liquid composition from which it was prepared. The solid composition was prepared having the following composition:

| Raw Material Type | Batch Size - 1000.00 g | Formula wt. % |
|---|---|---|
| Apple Fibre (Braeburn) - Fresh | 271.43 | 27.14 |
| Water - Tap | 50.00 | 5.00 |
| Sodium Lauryl Sulphate - Needles | 331.14 | 33.11 |
| Granulated Sugar | 108.57 | 10.86 |
| FD&C Yellow No 5 - 10% solution | 21.71 | 2.17 |
| Fragrance | 40.71 | 4.07 |
| Smectite Clay | 61.07 | 6.11 |
| Cellulose | 115.37 | 11.54 |
| | 1000.00 | 100.00 |

The dehydrated product was a sheet product that was pliable and foldable.

Comparison Study (Examples 6 and 7, and Comparative Examples 1 to 4)

A number of liquid compositions having the following compositions were prepared:

| Component | Ex. 6 | Ex. 7 | Comp. Ex. 1 | Comp. Ex. 2 | Comp. Ex. 3 | Comp. Ex. 4 |
|---|---|---|---|---|---|---|
| Melon Pulp (Honeydew) | 79.90% | 0.00% | 79.90% | 0.00% | 79.90% | 0.00% |
| Apple Pulp (Braeburn) | 0.00% | 39.95% | 0.00% | 39.95% | 0.00% | 39.95% |
| Water | 0.09% | 39.95% | 0.09% | 39.95% | 0.09% | 39.95% |
| Sodium Lauryl Sulphate | 14.00% | 14.00% | 0.00% | 0.00% | 17.00% | 17.00% |
| Hydroxypropyl methylcellulose | 2.00% | 2.00% | 0.00% | 0.00% | 0.00% | 0.00% |
| Sodium Polyacrylate | 1.00% | 1.00% | 0.00% | 0.00% | 0.00% | 0.00% |
| Fatty Acid Soap | 0.00% | 0.00% | 17.00% | 17.00% | 0.00% | 0.00% |
| Fragrance | 3.00% | 3.00% | 3.00% | 3.00% | 3.00% | 3.00% |
| FD&C Red 33 10% Solution | 0.10% | 0.10% | 0.10% | 0.10% | 0.10% | 0.10% |

Method:
2 batches of a solid surfactant composition were prepared in accordance with the present invention, comprising Honeydew melon fibres (Example 6) and Braeburn apple fibres (Example 7).

To demonstrate the importance of the surfactant and hydrocolloid combination, a fatty acid soap (consisting of an 80:20 ratio of sodium rapeseedate and sodium cocoate and >76% TFT) was added to 2 batches of the compositions according to the Examples 6 and 7, replacing the surfactant and hydrocolloid components, yielding Comparative Examples 1 and 2.

To further demonstrate the importance of the surfactant and hydrocolloid combination, the hydrocolloid was omitted from 2 batches of the compositions according to Examples 6 and 7, yielding Comparative Examples 3 and 4.

The solid cosmetic compositions according to Examples 6 and 7, and Comparative Examples 1 to 4 were prepared in accordance with the method of Example 3 disclosed above. After the solid cosmetic compositions were removed from their respective trays, individual samples were prepared (20 mm strips were cut for separate assessments) and tested to demonstrate the advantages of Examples 6 and 7 over each of Comparative Examples 1 to 4. Each of the compositions were tested using the following subjective criteria:

Appearance—Whether there were any physical defects that could be attributed to the composition itself, e.g. even surface, smoothness, mottling.

Flexibility—Ability of the composition to be folded in half and return to its original state without becoming damaged.

Wettability—Ability of the composition to be submerged in water and subsequently maintain structural integrity after removal. Compositions were submerged in water for 15 seconds and then held horizontally for 15 seconds. If breakage occurred the composition failed the wettability assessment.

Skin Sensation—Effect of the composition on the user, e.g. cleansing observations, foaming ability, sensory response and structural integrity during use.

Observations:

Example 6 had dried sufficiently after 6 hrs at 35° C.

Example 7, and Comparative Examples 3 and 4 required further drying for 2 hrs at 35° C.

Comparative Examples 1 and 2 required further drying for 4 hrs at 35° C. The finished product was slightly tacky to touch when removed from silicone tray.

Comparative Examples 3 and 4 separated during the dehydrating phase and could not be removed intact. The compositions were thus classified as failures. However, effort was made to assess sections of the compositions that could be removed.

Detailed observations for each of the Examples and Comparative Examples are provided in the Table below.

Comparative Examples 1 and 2 produced a solid composition that had good structural integrity when wet, although rapidly disintegrated when washed over skin. The drying effect of soap implies that these compositions are not suitable for sensitive skin and hair. The finished products were poor, failing the flexibility test, whilst discolouration was observed during use.

Comparative Examples 3 and 4 failed the flexibility, wettability and sensation tests and yielded a poor finished product.

Various modifications and variations of the present invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry, biology or related fields are intended to be within the scope of the following claims.

The invention claimed is:

1. A solid surfactant cosmetic composition comprising
   (i) insoluble fruit fibre, wherein the fruit fibre is obtained from melon or apple;
   (ii) synthetic surfactant; and

|  | Example No | | | | | |
|---|---|---|---|---|---|---|
|  | 1 | 2 | 3 | 4 | 5 | 6 |
| Appearance | Composition was smooth and firm to touch. Good colour distribution, although slight mottling observed. | Composition was smooth and sponge-like to touch, with excellent colour distribution throughout. | Composition was heavily pitted, but smooth and sponge-like to touch. Heavy mottling and significant colour variation was observed. | Composition was heavily pitted, but smooth and sponge-like to touch. Heavy mottling and significant colour variation was observed. | Composition produced a rough, uneven texture when dry. Significant colour variation. | Composition produced a rough, uneven texture when dry. Satisfactory colour uniformity. |
| Flexibility | Bent to 180° and returned to original orientation. Composition remained intact and in original condition. | Bent to 180° and returned to original orientation. Slight discolouration along folding axis, although sample remained intact. | After 3 attempts composition could be folded by >90°, but fractured when folded to 180°. | after 3 separate attempts the composition could not be folded by more than 90°. | After 3 separate attempts the composition could not be folded by more than 90°. | After 3 separate attempts the composition could not be folded by more than 90°. |
| Wettability | Excellent stability, with no breakage or bending when removed from water. | Excellent stability, with no breakage and little bending when removed from water | Good stability when wet, with no breakage. Slight discolouration and shrinkage was observed. | Good stability when wet, with no breakage. Slight discolouration and shrinkage was observed. | Composition disintegrated when submerged in water. | Composition disintegrated after removing from water. |
| Skin Sensation | Good lather formed, with a smooth sensation when washed between hands for 30 seconds. Composition remained intact throughout. | Good lather formed, with a smooth sensation when washed between hands for 30 seconds. Composition remained intact throughout. | Good lather formed, however composition quickly disintegrated. Composition felt smooth and soft to touch, but left skin feeling dry. | Good lather formed, however composition quickly disintegrated. Composition felt smooth and soft to touch, but left skin feeling dry. | Good lather formed, however composition quickly disintegrated and felt rough on the skin. | Good lather formed, however composition quickly disintegrated and felt rough on the skin. |

Summary of Results:

Examples 6 and 7 in accordance with the present invention were found to have superior properties compared with each of Comparative Examples 1 to 4.

Examples 6 and 7 both produced a high quality finished product that maintained excellent structural integrity when wet and washed over skin, whilst yielding a good lather and cleansing ability capable of washing all skin types and hair.

(iii) a hydrocolloid selected from the group consisting of cellulose, ethylcellulose, hydroxypropylmethylcellulose, methycellulose, hyrdroxyethylcellulose, hydroxypropylcellulose, sodium carbomethylcellulose, carboxymethylcellulose, calcium carboxymethylcellulose, alginate, pectin, xanthan, tragacanth and mixtures thereof;
   (iv) a thickener selected from the group consisting of sodium polyacrylate, starch, and mixtures thereof;

wherein the solid surfactant cosmetic composition is prepared by dehydrating a liquid composition comprising
(i) a fruit pulp containing insoluble fruit fibre, wherein the fruit pulp is in an amount of 55 to 99 wt. %, and wherein the fruit pulp is melon pulp or apple pulp;
(ii) synthetic surfactant in an amount of 0.9 to 40 wt. %;
(iii) hydrocolloid in an amount of 0.1 to 15 wt. %; and
(iv) a thickener selected from the group consisting of sodium polyacrylate, starch and mixtures thereof;
wherein the amounts are based on a total combined amount of pulp, synthetic surfactant and hydrocolloid.

2. A solid surfactant cosmetic composition according to claim 1, wherein the solid surfactant cosmetic composition is prepared by dehydrating a liquid composition comprising
(i) the fruit pulp in an amount of 65 to 95 wt. %; based on the total combined amount of pulp, surfactant and hydrocolloid.

3. A solid surfactant cosmetic composition according to claim 1 wherein the solid surfactant cosmetic comprises
(i) fruit pulp in an amount of 65 to 85 wt. %; based on the total combined amount of pulp, synthetic surfactant and hydrocolloid.

4. A solid surfactant cosmetic composition according to claim 1, wherein the fruit fibre is obtained from melon.

5. A solid surfactant cosmetic composition according to claim 1, wherein the fruit pulp containing insoluble fruit fibre is melon pulp.

6. A solid surfactant cosmetic composition according to claim 4 wherein the melon is honeydew melon.

7. A solid surfactant cosmetic composition according to claim 1, wherein the fruit fibre is obtained from apple.

8. A solid surfactant cosmetic composition according to claim 1, wherein the fruit pulp containing insoluble fruit fibre is apple pulp.

9. A solid surfactant cosmetic composition according to claim 1, wherein the solid surfactant cosmetic composition is prepared by dehydrating a liquid composition comprising
(ii) synthetic surfactant in an amount of 5 to 35 wt. %, based on the total combined amount of pulp, synthetic surfactant and hydrocolloid.

10. A solid surfactant cosmetic composition according to claim 1, wherein the solid surfactant cosmetic composition is prepared by dehydrating a liquid composition comprising
(ii) synthetic surfactant in an amount of 15 to 30 wt. %, based on the total combined amount of pulp, synthetic surfactant and hydrocolloid.

11. A solid surfactant cosmetic composition according to claim 1, wherein the synthetic surfactant is anhydrous.

12. A solid surfactant cosmetic composition according to claim 1, wherein the synthetic surfactant is selected from sodium lauryl sulphate, sodium cocoamphoacetate, sodium laureth sulphate, lauryl betaine, sodium lauroyl sarcosinate, sodium alkyl sulphate, disodium lauryl sulfosuccinate, disodium laureth sulfosuccinate, cocamide monoethanolamine, cetrimonium bromide and mixtures thereof.

13. A solid surfactant cosmetic composition according to claim 1, wherein the synthetic surfactant is anhydrous sodium lauryl sulphate.

14. A solid surfactant cosmetic composition according to claim 1, wherein the solid surfactant cosmetic composition is prepared by dehydrating a liquid composition comprising
(iii) hydrocolloid in an amount of 1 to 10 wt. %; based on the total combined amount of pulp, synthetic surfactant and hydrocolloid.

15. A solid surfactant cosmetic composition according to claim 1, wherein the solid surfactant cosmetic composition is prepared by dehydrating a liquid composition comprising
(iii) hydrocolloid in an amount of 0.5 to 10 wt. %; based on the total combined amount of pulp, synthetic surfactant and hydrocolloid.

16. A solid surfactant cosmetic composition according to claim 1, wherein the hydrocolloid is hydroxypropylcellulose.

17. A solid surfactant cosmetic composition according to claim 1, further comprising at least one additional component selected from binders, fillers, opacifiers, perfumes, colours, fragrances, decorative items, herbs and mixtures thereof.

18. A solid surfactant cosmetic composition according to claim 1, further comprising at least one additional component selected from colours, fragrances, herbs and mixtures thereof.

19. A solid surfactant cosmetic composition according to claim 1 wherein the combined amount of colours and fragrances is from 0.001 to 5 wt. % based on the total weight of the solid composition.

20. A solid surfactant cosmetic composition according to claim 1, further comprising sugar.

21. A solid surfactant cosmetic composition according to claim 18 wherein the sugar is present in an amount of 2 to 20 wt. %, based on the total combined amount of pulp, synthetic surfactant, hydrocolloid and sugar.

22. A solid surfactant cosmetic composition comprising
(i) insoluble fruit fibre in an amount of 20 to 85 wt. % based on a total combined amount of fibre, synthetic surfactant and hydrocolloid, wherein the insoluble fruit fibre is obtained from melon or apple;
(ii) synthetic surfactant in an amount of 20 to 75 wt. % based on the total combined amount of fibre, synthetic surfactant and hydrocolloid; and
(iii) hydrocolloid in an amount of 0.4 to 20 wt. % based on the total combined amount of fibre, synthetic surfactant and hydrocolloid, wherein the hydrocolloid is selected from the group consisting of cellulose, ethylcellulose, hydroxypropylmethylcellulose, methycellulose, hyrdroxyethylcellulose, hydroxypropylcellulose, sodium carbomethylcellulose, carboxymethylcellulose, calcium carboxymethylcellulose, alginate, pectin, xanthan, tragacanth and mixtures thereof; and
(iv) a thickener selected from the group consisting of sodium polyacetate, starch, and mixtures thereof; wherein the thickener is present in an amount of 1 to 50 wt. % based on a total weight of the solid composition.

23. A solid surfactant cosmetic composition comprising
(i) melon fibre;
(ii) synthetic surfactant;
(iii) a hydrocolloid selected from the group consisting of cellulose, ethylcellulose, hydroxypropylmethylcellulose, methylcellulose, hyrdroxyethylcellulose, hydroxypropylcellulose, sodium carbomethylcellulose, carboxymethylcellulose, calcium carboxymethylcellulose, alginate, pectin, xanthan, tragacanth and mixtures thereof;
(iv) a thickener selected from the group consisting of sodium polyacetate, starch, and mixtures thereof;
wherein the solid surfactant cosmetic composition is prepared by dehydrating a liquid composition comprising:
(i) melon;
(ii) the surfactant;

(iii) the hydrocolloid; and
(iv) the thickener.

24. A solid surfactant cosmetic composition comprising
(i) apple fibre;
(ii) a synthetic surfactant;
(iii) a hydrocolloid selected from the group consisting of cellulose, ethylcellulose, hydroxypropylmethylcellulose, methycellulose, hyrdroxyethylcellulose, hydroxypropylcellulose, sodium carbomethylcellulose, carboxymethylcellulose, calcium carboxymethylcellulose, alginate, pectin, xanthan, tragacanth and mixtures thereof; and
(iv) a thickener selected from the group consisting of sodium polyacetate, starch, and mixtures thereof;
wherein the solid surfactant cosmetic composition is prepared by dehydrating a liquid composition comprising:
(i) apple;
(ii) the surfactant;
(iii) the hydrocolloid; and
(iv) the thickener.

25. A solid surfactant cosmetic composition comprising
(i) apple fibre;
(ii) synthetic surfactant;
(iii) a hydrocolloid selected from the group consisting of cellulose, ethylcellulose, hydroxypropylmethylcellulose, methycellulose, hyrdroxyethylcellulose, hydroxypropylcellulose, sodium carbomethylcellulose, carboxymethylcellulose, calcium carboxymethylcellulose, alginate, pectin, xanthan, tragacanth and mixtures thereof; and
(iv) a thickener selected from the group consisting of sodium polyacetate, starch, and mixtures thereof;
wherein the solid surfactant cosmetic composition is prepared by dehydrating a liquid composition comprising:
(i) apple in an amount of from 20 to 75 wt. %;
(ii) synthetic surfactant in an amount of 0.9 to 40 wt. %;
(iii) hydrocolloid in an amount of 0.1 to 15 wt. %; and
(iv) a thickener selected from the group consisting of sodium polyacetate, starch, and mixtures thereof;
wherein the amounts are based on the total amount of the liquid composition.

26. A solid surfactant cosmetic composition according to claim 24, wherein the solid surfactant cosmetic composition is prepared by dehydrating a liquid composition comprising
(i) the apple in an amount of 30 to 40 wt. %, based on the total amount of the liquid composition.

27. A cosmetic method comprising contacting the skin or hair of a user with water into which is dissolved a solid surfactant cosmetic composition as defined in claim 1.

* * * * *